United States Patent
Kim et al.

(10) Patent No.: US 10,058,079 B2
(45) Date of Patent: Aug. 28, 2018

(54) INTERLEUKIN 2 RECEPTOR GAMMA GENE TARGETING VECTOR, PRODUCTION OF IMMUNE CELL-DEFICIENT TRANSGENIC CLONED MINI PIG HAVING VECTOR INTRODUCED THEREIN, PREPARATION METHOD THEREFOR AND USE THEREOF

(71) Applicants: KONKUK UNIVERSITY INDUSTRIAL COOPERATION CORP., Seoul (KR); THE CURATORS OF THE UNIVERSITY OF MISSOURI, Columbia, MO (US)

(72) Inventors: Jin-Hoi Kim, Seoul (KR); Deug-Nam Kwon, Seoul (KR); Kiho Lee, Columbia, MO (US); Randall S. Prather, Columbia, MO (US)

(73) Assignees: KONKUK UNIVERSITY INDUSTRIAL COOPERATION CORP., Seoul (KR); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/036,550

(22) PCT Filed: Nov. 13, 2014

(86) PCT No.: PCT/KR2014/010897
§ 371 (c)(1),
(2) Date: May 13, 2016

(87) PCT Pub. No.: WO2015/072761
PCT Pub. Date: May 21, 2015

(65) Prior Publication Data
US 2016/0366861 A1   Dec. 22, 2016

(30) Foreign Application Priority Data

Nov. 13, 2013   (KR) .................. 10-2013-0137675

(51) Int. Cl.
| | |
|---|---|
| *A01K 67/00* | (2006.01) |
| *A01K 67/027* | (2006.01) |
| *C12N 15/877* | (2010.01) |
| *C12N 5/077* | (2010.01) |
| *G01N 33/483* | (2006.01) |
| *G01N 33/569* | (2006.01) |

(52) U.S. Cl.
CPC ........ *A01K 67/0276* (2013.01); *C12N 5/0656* (2013.01); *C12N 15/8778* (2013.01); *G01N 33/483* (2013.01); *G01N 33/56977* (2013.01); *A01K 2217/075* (2013.01); *A01K 2227/108* (2013.01); *A01K 2267/03* (2013.01); *A01K 2267/0387* (2013.01); *C12N 2510/00* (2013.01); *G01N 2333/7155* (2013.01)

(58) Field of Classification Search
CPC .......... A01K 67/0276; A01K 2227/108; C12N 5/0656
See application file for complete search history.

(56) References Cited

U.S. PATENT DOCUMENTS

| | | | |
|---|---|---|---|
| 2012/0222143 A1 | 8/2012 | Fahrenkrug et al. | |
| 2016/0366860 A1 | 12/2016 | Kim et al. | |

FOREIGN PATENT DOCUMENTS

| | | |
|---|---|---|
| CN | 103184202 A | 7/2013 |
| KR | 10-2004-0074108 A | 8/2004 |
| KR | 10-1312829 B1 | 9/2013 |
| WO | 2012/116274 A2 | 8/2012 |
| WO | 2015/168125 A1 | 11/2015 |

OTHER PUBLICATIONS

Daniel F. Carlson et al., "Efficient TALEN-mediated gene knockout in livestock," PNAS, Oct. 23, 2012, vol. 109, No. 43, pp. 17382-17387.
Daniel F. Carlson et al., "Supporting information," PNAS, 10.1073/pnas.1211446109, 2012, pp. 1-9.
Database Geneseq, "Human IL2RG gene fragment (exon 2)," Jan. 30, 2014, XP002767475, retrieved from EBI accession No. GSN:BBA51186, Database accession No. BBA51186, the whole document. The query sequence SEQ ID No. 1 has 98.00% identity over 50 positions in common overlap (range (q:s): 1-50:11-60) with subject GSN: BBA51186 (length : 65) from CN103184202-A published on Jul. 3, 2013.
Extended European Search Report in European Patent Application No. 14862785.4, dated Mar. 10, 2017.
Rebecca H. Buckley, "Molecular Defects in Human Severe Combined Immunodeficiency and Approaches to Immune Reconstitution," Annu. Rev. Immunology 2004, vol. 22, pp. 625-655.
Jeffrey J. Whyte et al., "Genetic Modifications of Pigs for Medicine and Agriculture," Molecular Reproduction & Development, 2011, vol. 78(10-11), pp. 879-891.
Xlqing Cao et al., "Defective Lymphoid Development in Mice Lacking Expression of the Common Cytokine Receptor y Chain," Immunity, vol. 2, Mar. 1995, pp. 223-238.
Shunichi Suzuki et al., "Il2rg Gene-Targeted Severe Combined Immunodeficiency Pigs," Cell Stem Cell vol. 10, Jan. 14, 2012, pp. 753-758.
Masahito Watanabe et al., "Generation of Interleukin-2 Receptor Gamma Gene Knockout Pigs from Somatic Cells Genetically Modified by Zinc Finger Nuclease-Encoding mRNA," PLOS One, vol. 8, Issue 10, Oct. 2013.
Hyojin Kim et al., "Magnetic Separation and Antibiotics Selection Enable Enrichment of Cells with FN/TALEN-Induced Mutations," PLOS One, vol. 8, Issue 2, Feb. 2013.
Jun Song et al., "Generation of RAG 1- and 2-deficient rabbits by embryo microinjection of TALENs," Cell Research, 2013, vol. 23, pp. 1059-1062.

(Continued)

*Primary Examiner* — Marcia S Noble
(74) *Attorney, Agent, or Firm* — Baker & Hostetler LLP

(57) ABSTRACT

The present invention relates to an interleukin-2 receptor gamma (IL2RG) gene-targeting vector, a method for producing an immune cell-deficient transgenic cloned miniature pig having the vector introduced therein, and the use thereof.

5 Claims, 16 Drawing Sheets

Specification includes a Sequence Listing.

(56) References Cited

OTHER PUBLICATIONS

Kiho Lee et al., "Engraftment of human iPS cells and allogeneic porcine cells into pigs with inactivated RAG2 and accompanying severe combined immunodeficiency," PNAS, vol. 111, No. 20, May 20, 2014.
J. Huang et al., "RAG1/2 Knockout Pigs with Severe Combined Immunodeficiency," The Journal of Immunology, vol. 193, 2014, pp. 1496-1503.
Extended European Search Report in European Patent Application No. 14862841.5, dated Mar. 24, 2017.
Anna Villa et al., "Omenn Syndrome: A Disorder of Rag 1 and Rag 2 Genes," Journal of Clinical Immunology, 1999.
Yoichi Shinkai et al., "RAG-2-Deficient Mice Lack Mature Lymphocytes Owing to Inability to Initiate V(D)J Rearrangement," Cell, 1992.

[FIG 1a]
IL2RG
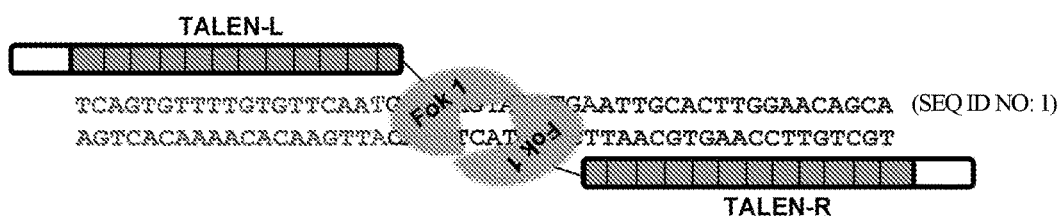
(SEQ ID NO: 1)
[FIG 1b]

[FIG 1c]
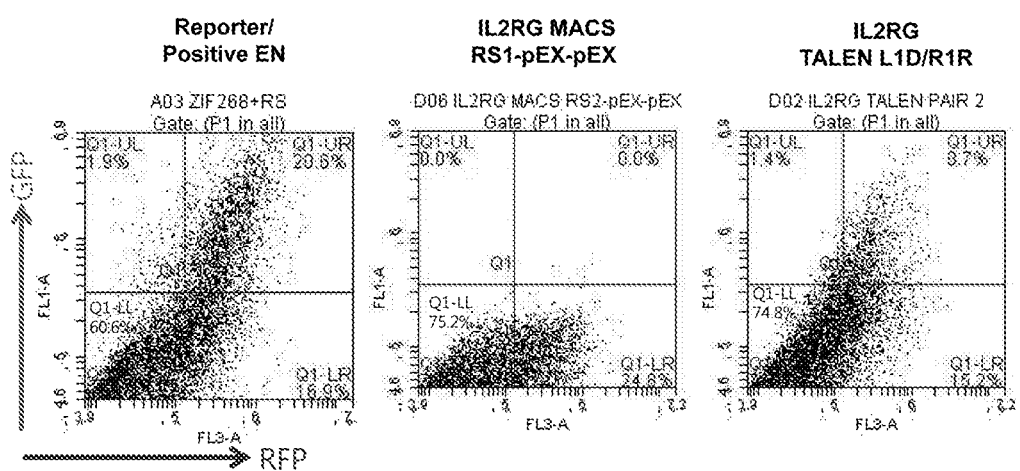

[FIG 1d]
IL2RG monoallelic
TCAGTGTTTTGTGTTCAATGTTGAGTACATGAATTGCACTTGGAACAGCA (SEQ ID NO: 1)
TCAGTGTTTTGTGTTCAATGTTGAG------- TGAATTGCACTTGGAACAGCA (SEQ ID NO: 24)
[FIG 2]
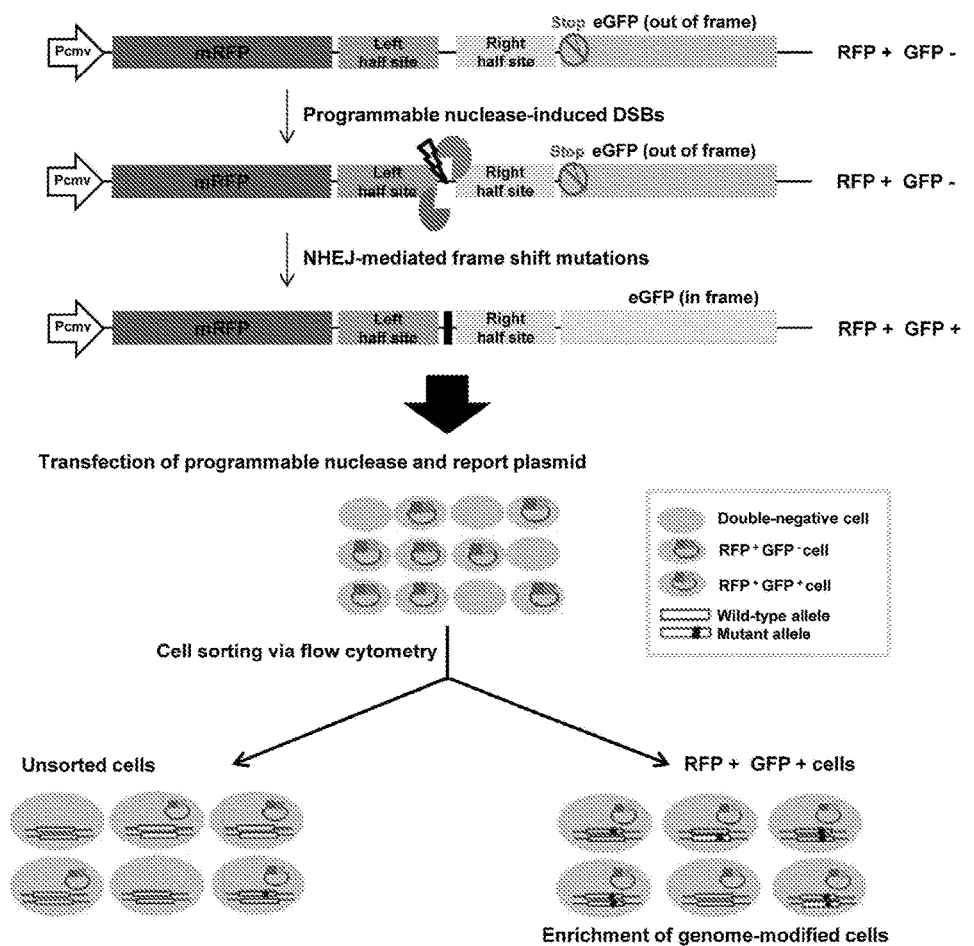

[FIG 3a]
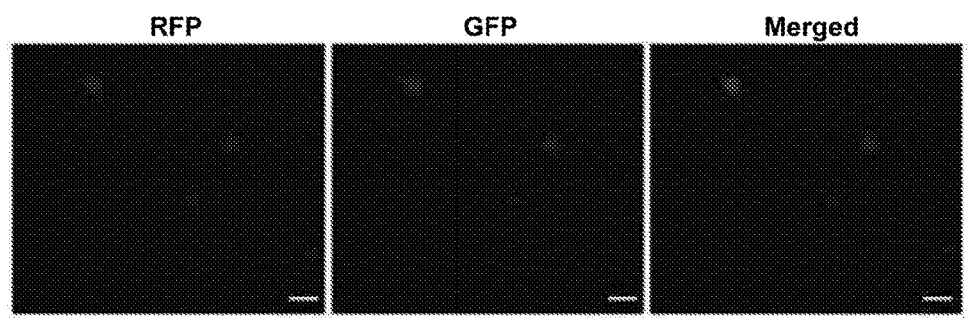

【FIG 3b】

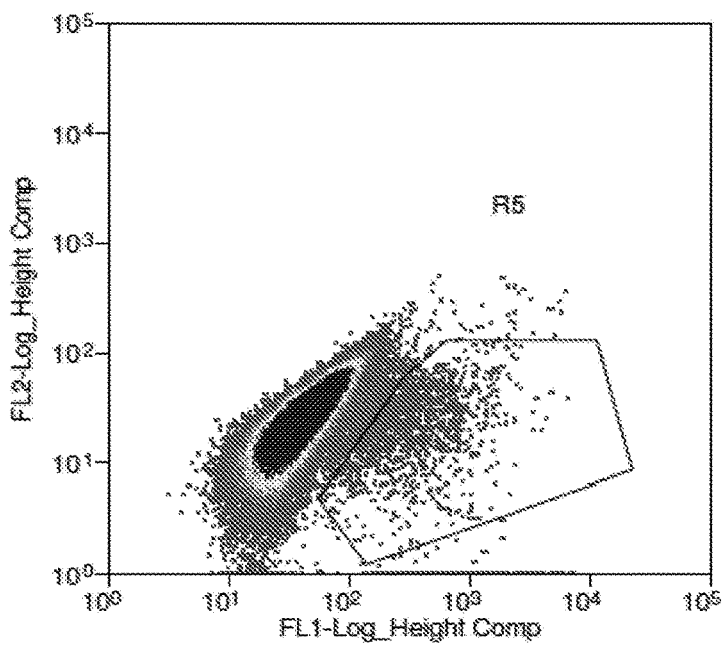

【FIG 4】

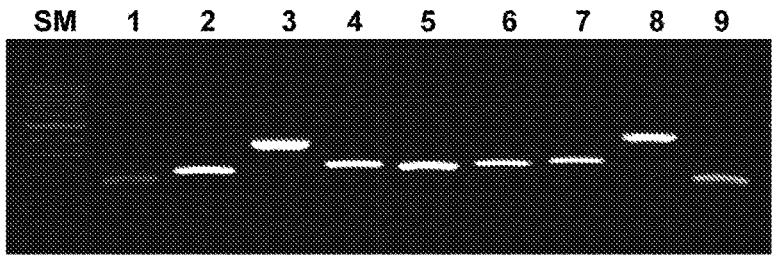

| Gene | Sequence | |
|---|---|---|
| IL2RG | TCAGTGTTTTGTGTTCAATgttgagtacatgAATTGCACTTGGAACAGCA | (SEQ ID NO:25) |
| LRRIQ1 | ATAATGCAGCTGTAAAAATcaagctaaataTAAAGCACTTGTGGCCTAC | (SEQ ID NO:26) |
| BNC2 | TCAGTGTTTTGTGTTTCCCccacatgatgtgTCAGAAACGAAAGCCAGCC | (SEQ ID NO:27) |
| SLC17A5 | TTCTTGTTTTGTCCTGTTTgttcaacactacCTGTAACATTTTAACTAAA | (SEQ ID NO:28) |
| ZNF334 | TCAGTGTGGAAAATTTTTAtgtactgaagcaGCCCTCATGGCACATCAGA | (SEQ ID NO:29) |
| TTN | CTACGATGGTGGTGGAATGgctccacgatggAAAGCCACTTG--AAGCAGC | (SEQ ID NO:30) |
| PGRMC2 | TTGGGGTTTTGTCAGGGAAagaaaaaactTATTTCTAAGAAATCTTTG | (SEQ ID NO:31) |
| AVPR2 | GAAGCGGTAGCTGGCATCCcaggccagctggGGCAGCACTTGGAACAGAG | (SEQ ID NO:32) |
| CCDC18 | CTTTCTGAAGAATTATTGCaggacttaaaaaAAATGCAACTGGAACAACC | (SEQ ID NO:33) |
| ZSWIM2 | TTATATATAACTTGTCCATcaatagggcatgAATTGCATTGGTGGAATAA | (SEQ ID NO:34) |

[FIG 5]
Wild type
IL2RG
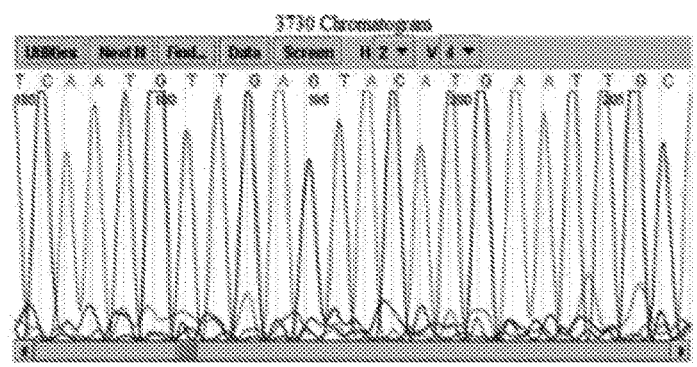
Targeted
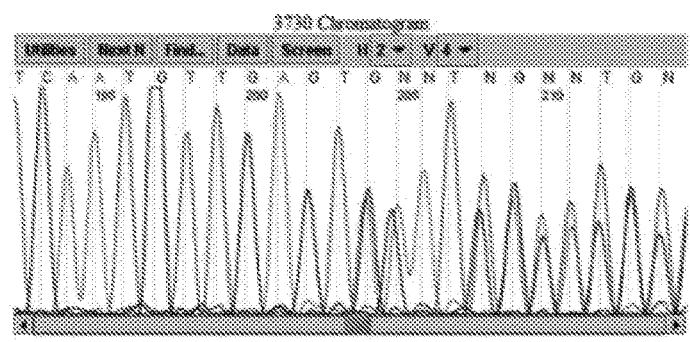

[FIG 6]
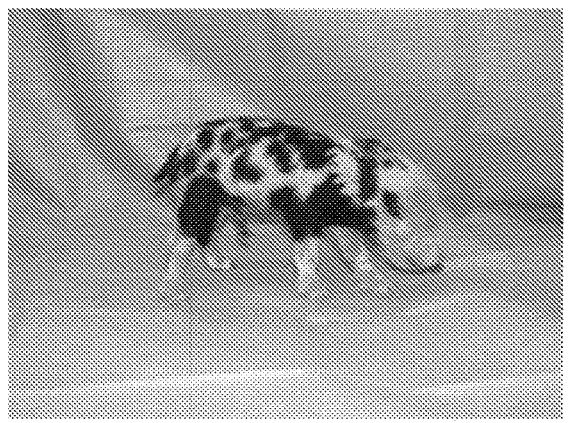
*IL2RG*
[FIG 7]
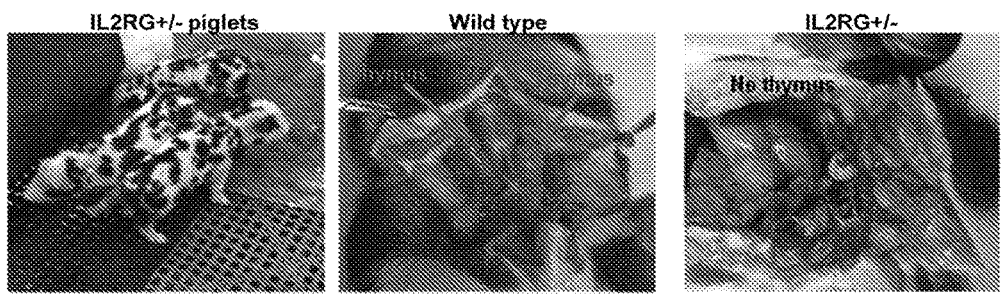

【FIG 8a】
IL2Rα
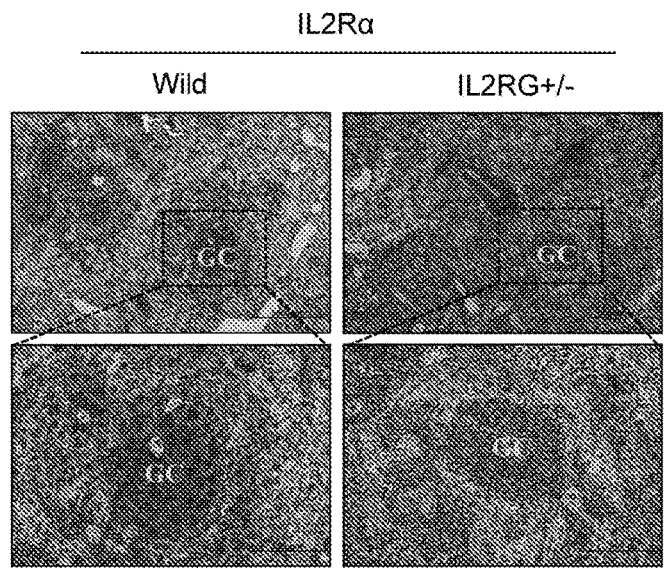
【FIG8b】
IL2Rγ
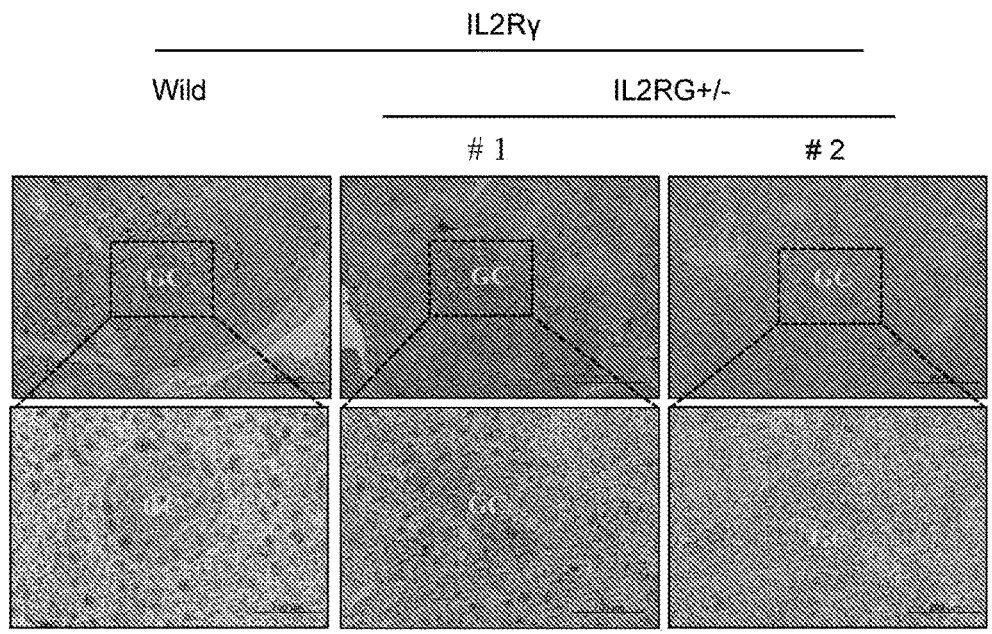

[FIG 8c]
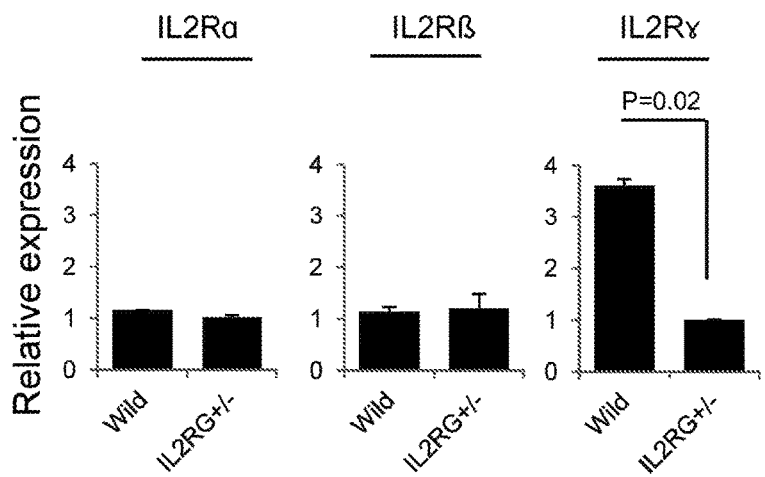
[FIG 9a]
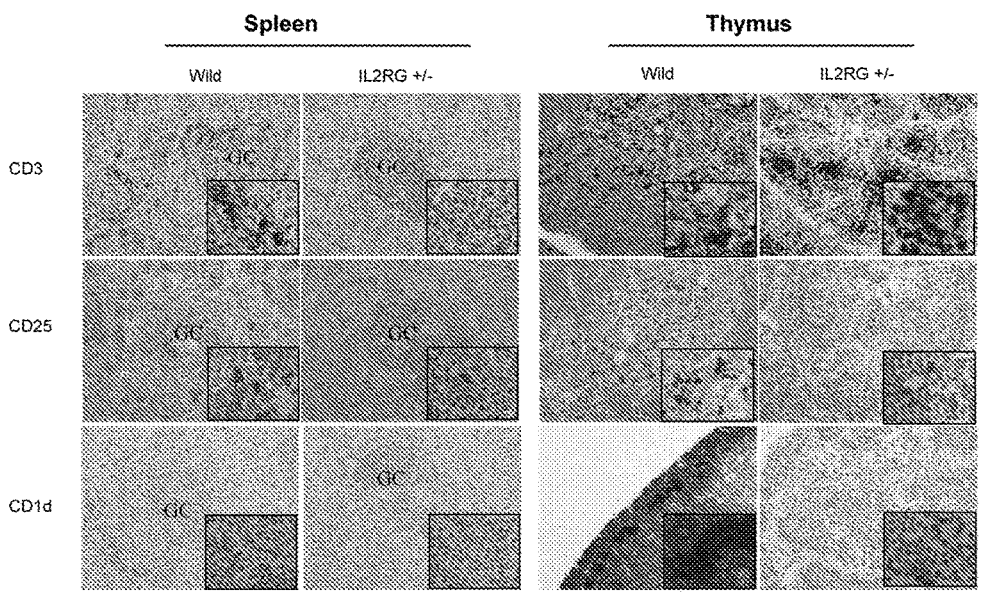

[FIG 9b]
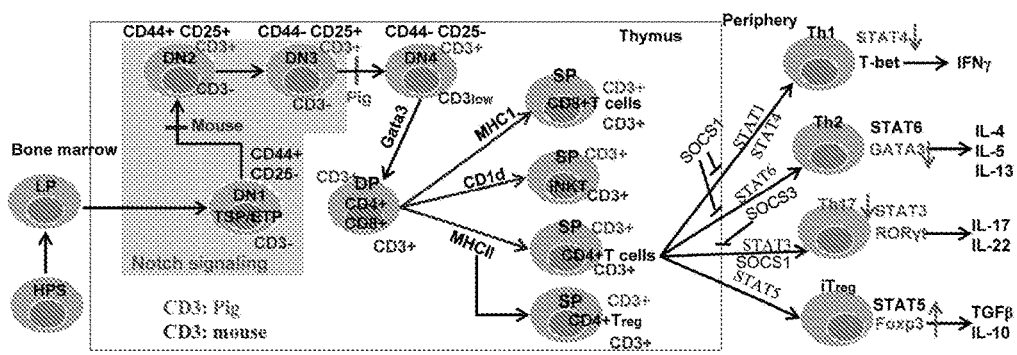

[FIG 10a]
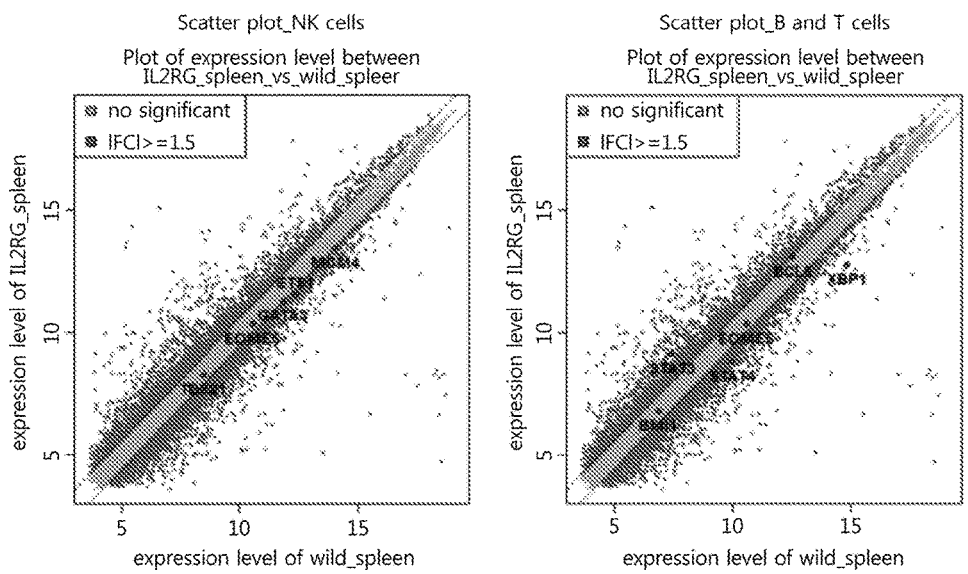

[FIG 10b]
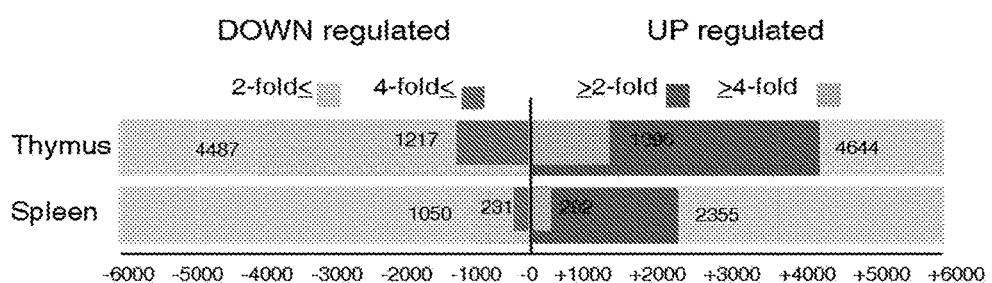

[FIG 10c]
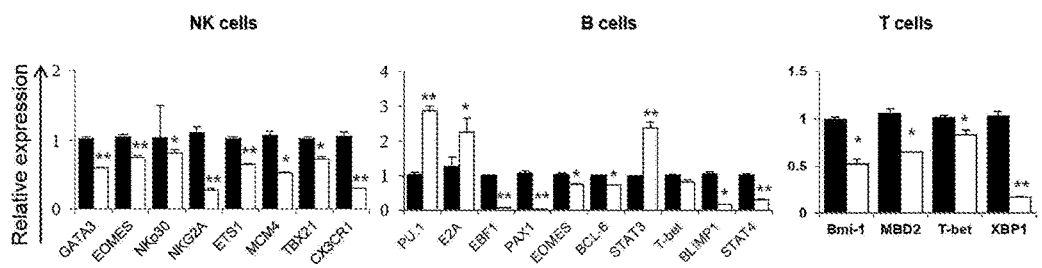

【FIG 10d】
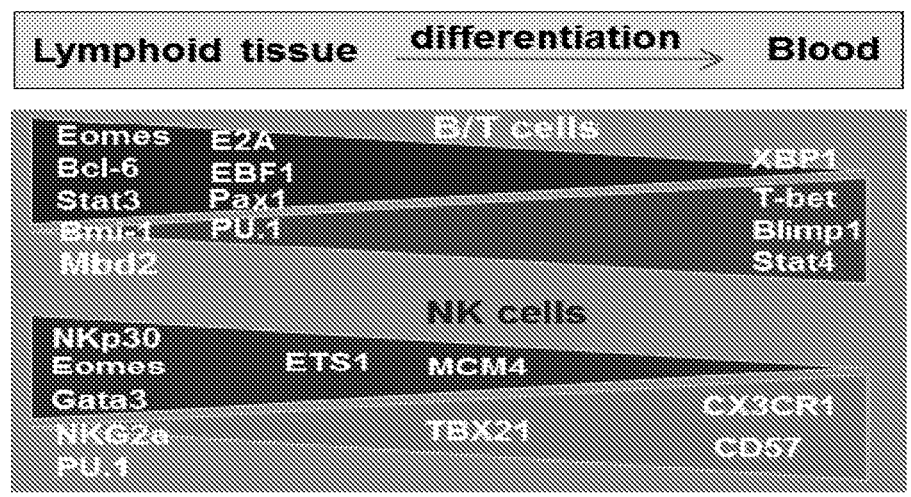
【FIG 11a】
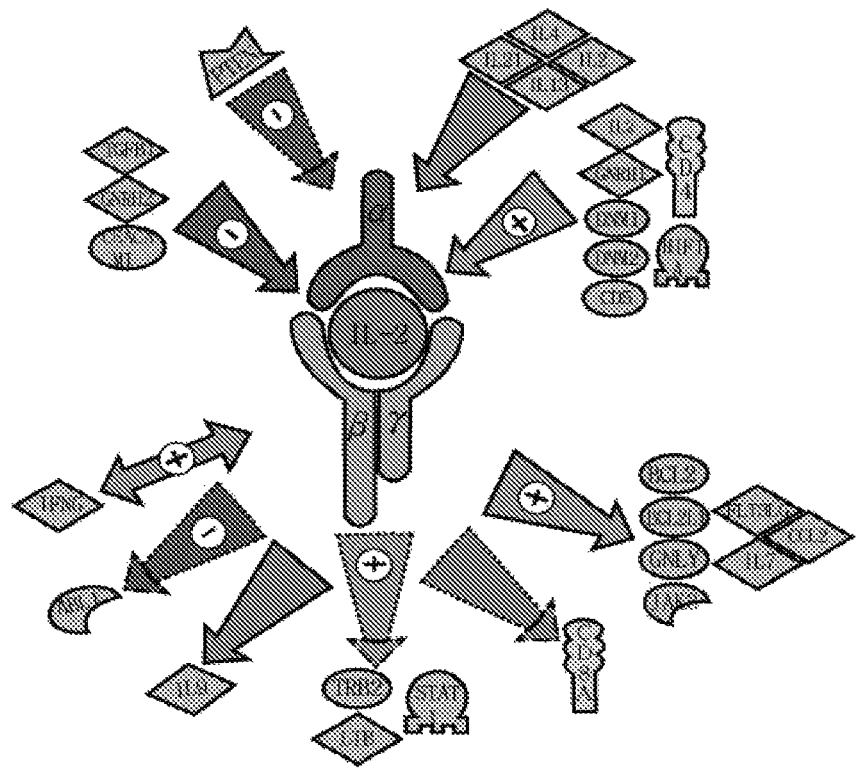

[FIG 11b]
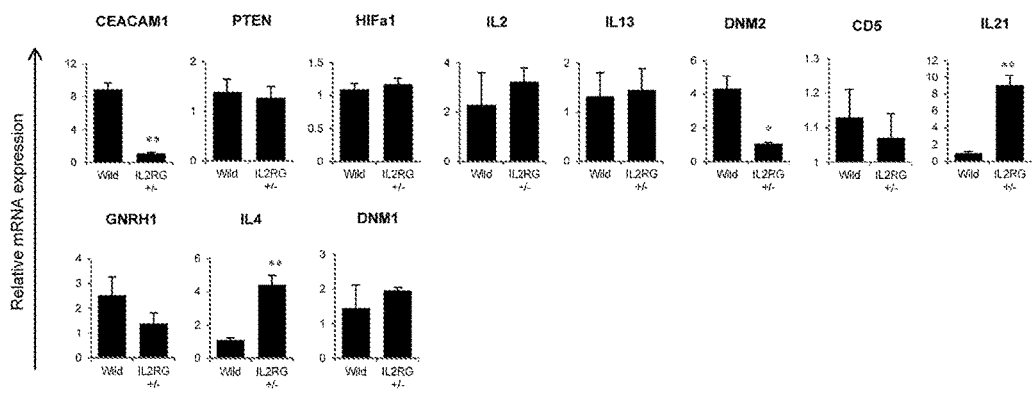

[FIG 11c]
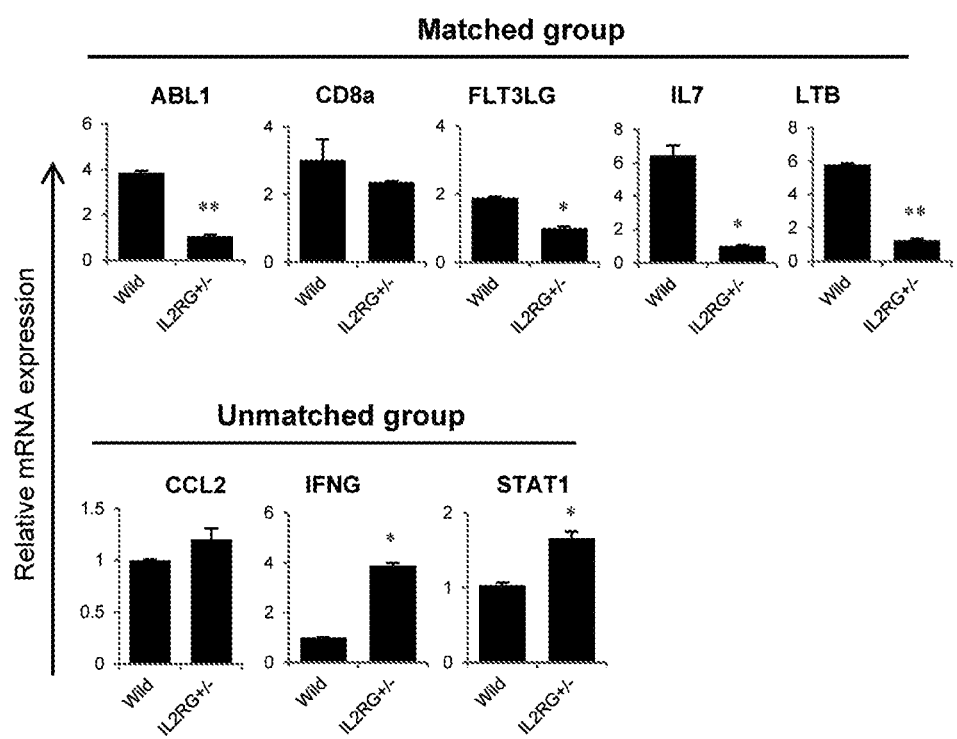

INTERLEUKIN 2 RECEPTOR GAMMA GENE TARGETING VECTOR, PRODUCTION OF IMMUNE CELL-DEFICIENT TRANSGENIC CLONED MINI PIG HAVING VECTOR INTRODUCED THEREIN, PREPARATION METHOD THEREFOR AND USE THEREOF

CROSS-REFERENCE TO RELATED APPLICATIONS

This application is the National Stage of International Patent Application No. PCT/KR2014/010897, filed Nov. 13, 2014, which claims the benefit of Korean patent application number KR 10-2013-0137675, filed Nov. 13, 2013, the disclosures of which are incorporated herein by reference in their entireties.

SEQUENCE LISTING

The instant application contains a sequence listing which has been submitted electronically in ASCII format and is hereby incorporated by reference in its entirety. The ASCII copy, entitled 087248_003380_SL.txt, was created on Aug. 31, 2016, is 8,045 bytes in size.

TECHNICAL FIELD

The present invention relates to an interleukin-2 receptor gamma (IL2RG) gene-targeting vector, a method for producing an immune cell-deficient transgenic cloned miniature pig having the vector introduced therein, and the use thereof.

BACKGROUND ART

Severe combined immunodeficiency (hereinafter referred to as 'SCID') occurs in humans (Buckley, R. H. *Annual review of immunology* 22, 625-655 (2004)). However, an agent for treating SCID was not easily developed due to limited animal models reflecting the type of human SCID. Pigs have physiological characteristics similar to those of humans, and mimic many human diseases with a similarity higher than rodent models (Whyte, J. J. & Prather, R. S. *Molecular reproduction and development* 78, 879-891 (2011)). Thus, SCID pigs can represent models that mimic human diseases. In addition, SCID pig models can be used in cancer research, cell transplantation, and drug development research.

Interleukin 2 receptor gamma (hereinafter referred to as 'IL2RG') is associated with X-linked SCID types, and IL2RG mutations cause deficiency of T and NK cells and functionally impaired B cells in mice (Cao, X. et al. *Immunity* 2, 223-238 (1995)). X-linked SCID pigs generated by disruption of IL2RG were recently reported, which exhibit human X-linked SCID phenotypes (Suzuki, S. et al. *Cell stem cell* 10, 753-758 (2012)).

Prior Art Documents

Korean Laid-Open Patent Publication No. 10-2004-0074108.

DISCLOSURE

Technical Problem

The present invention has been made in view of the above need, and an object of the present invention is to provide an effective method for producing a genetically engineered pig that exhibits SCID phenotypes.

Technical Solution

To achieve the above object, the present invention provides a method for producing an immune cell-deficient transgenic cloned miniature pig having an allelic mutation in interleukin-2 receptor gamma (IL2RG), the method comprising the steps of: treating the TALEN (transcription activator-like effector nuclease) recognition sequence site of chromosome X of a pig (*Sus scrofa*), which is represented by SEQ ID NO: 1, with TALEN to induce an allelic mutation; and producing mutant embryos by somatic cell nuclear transfer (SCNT) using cells having the induced allelic mutation.

In an embodiment of the present invention, the treatment of the TALEN recognition sequence site with the TALEN is preferably performed by transfecting the cells of interest with a vector encoding the TAL effector nuclease, but is not limited thereto.

The present invention also provides an immune cell-deficient transgenic cloned miniature pig having an allelic mutation in interleukin-2 receptor gamma (IL2RG), produced by the production method of the present invention.

The present invention also provides a method for sorting cells, comprising: introducing into cells a TAL effector nuclease-encoding vector capable of recognizing the TALEN recognition sequence site of chromosome X of a pig (*Sus scrofa*), which is represented by SEQ ID NO: 1, to induce mutation in the gene sequence of interest or a region flanking the gene sequence, together with a reporter vector comprising a monomeric red fluorescent protein (RFP) gene, a targeting sequence of programmable nuclease as set forth in SEQ ID NO: 1, an enhancer green fluorescent protein (GFP) and an H-2KK gene; and sorting cells, which are positive for the RFP, the GFP and the H-2KK, as interleukin-2 receptor gamma (IL2RG)-targeted cells.

In an embodiment of the present invention, detection of the H-2KK is preferably performed by an antibody.

In another embodiment of the present invention, expression of the RFP and the GFP is preferably detected by flow cytometry, but is not limited thereto.

The present invention also provides cells having an allelic mutation induced by treating the TALEN (transcription activator-like effector nuclease) recognition sequence site of chromosome X of a pig (*Sus scrofa*), which is represented by SEQ ID NO: 1, with TALEN.

The cells of the present invention was deposited with the Korean Collection for Type Cultures, Korea Research Institute of Bioscience and Biotechnology (Yuseong-gu, Daejeon, South Korea) on Oct. 2, 2013 under accession number KCTC 12497BP.

Hereinafter, the present invention will be described.

In the present invention, the present inventors report an effective method in which two types of genetically engineered pigs that exhibit SCID phenotypes are produced using transcription activator-like effector nuclease (TALEN)-mediated targeting with somatic cell nuclear transfer (SCNT).

In order to target porcine IL2RG, specific TALENs were designed and synthesized by ToolGen (Seoul, South Korea). Each of the TALENs was designed to cause a mutation on chromosome X of IL2RG (FIG. 1*a*). A reporter including a TALEN recognition site was used to identify cells that properly express a TALEN set (FIGS. 3 and 1*b*). The activities of the designed TALENs were confirmed by inserting a TALEN set with the reporter into HEK 293T cells (FIG. 1c). After confirmation, constructs encoding the TALENs and the reporter were inserted into porcine fibroblasts by electroporation. After 48 hours, the cells were sorted for GFP-positive cells (FIG. 3), and plated into a 96-well plate at a density of one cell per well. After 10 days, the cells were subcultured, and half of the cells were used for genotyping.

Sequencing of small PCR fragments (about 400 bp) flanking the predicted TALEN cleavage site showed the presence of a TALEN-induced insertion/deletion (indel) in the IL2RG group; a total of 30 colonies were screened for IL2RG (see primer information in Table 1 below). The efficiency of gene targeting was 30% (9/30) for IL2RG.

The TALENs used in the present invention were specific for their targets, and thus the present inventors could not observe off-target cleavage (FIG. 4 and Table 2). The targeting confirmed cells were used for somatic cell nuclear transfer (SCNT) (FIG. 5).

Mutant embryos were produced by SCNT, and 733 embryos were transferred into four surrogate gilts which were all found to be pregnant on day 25. One living IL2RG mutant was born (FIG. 6 and Table 3 below). Genotyping indicated that the pigs have targeted mutations of IL2RG (FIG. 1d). The mutation in IL2RG was a deletion of four nucleotides resulting in a premature termination codon (IL2RG+/Δ69-368).

FIG. 7 shows produced IL2RG+/− piglets and anatomical photographs of the produced IL2RG+/− piglets.

FIG. 8 shows the results of analyzing the expression of IL2R. As can be seen therein, it was found by real-time RT-PCR and IHC that the produced IL2RG+/− showed high target specificity and that, among IL2 receptors, IR2Rα and IR2Rβ were normally expressed and only IR2Rγ was influenced. To analyze the characteristics of IL2RG (+/−) heterozygote pigs, the protein expression of IL2RG in the spleen was analyzed. The expressions of IL2R alpha and IL2R gamma proteins in the spleens of the IL2RG+/− offspring were also analyzed. The expression of IL2 receptor alpha in the IL2RG+/− spleen was analyzed, and as a result, it was shown that IL2Ra was normally expressed in the wild type pig and the IL2RG+/− knockout pig. To reconfirm such results, the mRNA expressions of these genes were examined, and the results of the examination are as shown in FIG. 8c. These results were the same as the results of the protein expression. Namely, it could be seen that there was little or no difference in the expressions of IL-2R alpha and IL-2R beta between the wild type pig and the IL2RG+/− knock-out pig and that the expression of IL-2R gamma in the IL2RG+/− pig was at least four times lower than that in the wild type.

FIG. 9 shows the results of analyzing a subset of CD3+ T cells using T cell markers (CD25 and CD3). In addition, the T cell development process in porcine thymus was examined.

FIG. 10 shows the results of microarray chip analysis performed using IL2RG+/− tissue and normal tissue. Gene expressions in the spleen and the thymus were analyzed by a DNA chip assay and normalized to a control group, and then up- or down-regulated genes were determined.

As shown in FIG. 10, the control group showed a distinct difference in expression pattern from the IL2RG-knockout group. Interestingly, the difference in expression was more distinct in the thymus than in the spleen, and this appears to be because the development of the IL2RG KO pig thymus was very insignificant (FIG. 10a).

The greatest difficulty in DNA chip analysis of pigs is that the analysis of function between difference species is still impossible because the gene bank deposition of the sequences of functional genes for proteins is insufficient, even though the full-length genomic DNA sequence of pigs was reported. Thus, comparative analysis with mouse genes is used to overcome the limitation of porcine genome analysis. For this reason, in the present invention, only porcine genes that were functionally consistent with mouse genes were sorted. As a result, it was analyzed that genes down-regulated 2 folds or more were 4487 genes in the thymus and 1050 genes in the spleen and that genes down-regulated 4 folds or more were 1217 genes in the thymus and 231 genes in the spleen (FIG. 10b).

IL-2RG-knockout pigs show immunodeficiency. For this reason, in order to compare the expressions of genes associated with B, T and NK cells, the Studio pathway was analyzed using existing information reported for mice. Based on the results of the analysis, major genes involved in the development and differentiation of TB/NK cells were screened, and the expressions of these genes were examined. The results of the examination are as shown in FIG. 10c.

FIG. 11 shows factors that influence IL2 receptors, and factors that are influenced by IL2 receptors. In the case of a group of genes upstream of IL-2RG, CEACAM1, GNRH1, IL-4, DNM2 and IL21 genes were influenced by the IL-2RG gene so that the expressions of these genes were up- or down-regulated. Although further studies will be required, the results for these genes, which differ from those for the control, currently indicate that these genes play a direct or indirect role in the expression of IL-2RG while exchanging cis- or trans-signals. Among genes involved in signals downstream of IL-2RG, the results for the majority of the genes were consistent with the results analyzed by Pathway Studio Software, but the expressions of CCL2, IFNG and STAT1 genes were different from the results analyzed by Pathway Studio Software. This phenomenon would occur because (1) the IL-2RG-knockout (KO) pigs analyzed used heterozygotic organs, and (2) the gene expression mechanisms in the pigs were different from those in mice.

In the present invention, the present inventors have found that SCID pigs derived by SCNT can be effectively produced by TALEN-mediated gene targeting. The use of a reporter vector with a TALEN construct induced a high rate of mutation. Unlike conventional gene targeting in which a targeting vector is inserted into the genome, the present invention enables the production of genetically engineered pigs without leaving any feature in the genome. Genetically engineered pigs produced in the present invention can be used as models for SCID research, including a first pig model that can exhibit Omenn syndrome in humans (pigs are available from the National Swine Resource and Research Center).

Advantageous Effects

Pigs with a severe combined immunodeficiency (SCID) phenotype will be useful in stem cell therapy, cancer research, and xenograft development. The present inventors describe the production of two types of SCID pigs (IL2RG knockout) by TALEN-mediated targeting.

DESCRIPTION OF DRAWINGS

FIG. 1a, FIG. 1b, FIG. 1c, and FIG. 1d show the production of SCID pigs using TALENs. Specifically, FIG. 1(a) schematically shows TALEN-mediated knockout of IL2RG and RAG2 (SEQ ID NOs: 22 and 23, respectively, in order of appearance). FIG. 1(b) shows a donor reporter vector including a TALEN recognition site. Cleavage of the TALEN recognition site in the donor reporter vector induces the expression of GFP. FIG. 1(c) shows the results of confirming designed TALENs in vitro. The expression of GFP can be detected even when TALENs are transfected with the donor reporter gene in HEK 293T cells. FIG. 1(d) shows the genotype of a pig produced by a genetic engineering method (SEQ ID NOs: 1 and 24, respectively, in order of appearance).

FIG. 2 shows construction of a surrogate reporter vector for enrichment of cells targeted by TALENs. (a) The reporter vector comprises a monomeric RFP gene, a programmable nuclease-targeting sequence (left half-site and right half-site), an enhancer GFP and an H-2KK gene (the upper panel of FIG. 2). If the GFP and H-2KK sequences are out of the frame due to the absence of programmable nuclease activity, only the RFP gene is expressed. When double-strand cleavage by programmable nuclease is inserted into the targeting sequence, the cleavage is repaired by non-homologous end-joining (NHEJ), and often causes frame shift mutations. Such mutations can make GFP in frame with RFP, and induce the expression of an mRFP-eGFP-H-2KK fusion protein (lower panel of FIG. 2). (b) Two systems: magnetic separation by H-2KK antibody, and enrichment of nuclease-induced mutations in mRFP+eGFP+H-2KK+ cells sorted by flow cytometry according to the expressions of RFP and GFP. In cells, the reporter plasmid and the chromosome target site are shown. Mutations are indicated by black spots.

FIG. 3a and FIG. 3b show FACS sorting of GFP-positive cells after introduction of TALENs. FIG. 3(a) High co-expression of RFP and GFP after 48 hours of transfection. FIG. 3(b) The box below the arrow indicates GFP-positive cells. The top 10% cells expressing strong GFP were sorted and placed in a 96-well plate. GFP-positive cells ranged from 23.0% to 38.0%. Scale bar=20 μm.

FIG. 4 shows the off-target analysis of the IL2RG mutant porcine IL2RG gene. Top) treatment of heteroduplex DNA with Surveyor nuclease showed no additional off-target mutation in 9 loci having the highest homology with the IL2RG gene. SM: size marker, lane 1: LRRIQ1; 2: BNC2; 3: SLC17A5; 4: ZNF334; 5: TTN; 6: PGRMC2; 7: AVPR2.8: CCDC18; and 9: ZSWIM2. Bottom) genes having IL2RG-related sequences (SEQ ID NOs: 25-34, respectively, in order of appearance) for excluding off-target mutations, and sequence homology between the genes.

FIG. 5 shows the results of PCR sequencing for identifying candidate cell colonies for SCNT (SEQ ID NOs: 35 and 36, respectively, in order of appearance). Introduction of TALENs induced polymorphisms near the TALEN binding sites due to NHEJ. The types of polymorphisms were analyzed and used as cell colonies for SCNT.

FIG. 6 is an image of an SCID pig model produced in the present invention. The genetic background of the pig is a Minnesota mini-pig.

FIG. 7 shows produced IL2RG+/− piglets.

FIG. 8a, FIG. 8b, and FIG. 8c show the results of verifying the expression of IL2R.

FIG. 9a and FIG. 9b show the results of analyzing a subset of CD3+ T cells using T cell markers (CD25 and CD3).

FIG. 10a, FIG. 10b, FIG. 10c, and FIG. 10d show the results of microarray chip analysis performed using IL2RG+/− tissue and normal tissue.

FIG. 11a, FIG. 11b, and FIG. 11c show factors that influence IL2 receptors, and factors that are influenced by IL2 receptors.

MODE FOR INVENTION

Hereinafter, the present invention will be described in further detail by non-limiting examples. It is to be understood, however, that these examples are for illustrative purposes only and are not intended to limit the scope of the present invention.

All animals and experiments used in the present invention were approved by the Institutional Animal Care and Use Committee, University of Missouri.

Example 1: Cell Transfection and Gene Targeting

For gene targeting, 2-3 million cells were transfected with TALEN constructs having a reporter vector (2 μg of each construct/million cells). The cells were electroporated with the construct using a BTX Electro Cell Manipulator (Harvard Apparatus, Holliston, Mass.) at 490 V, 1 msec and 3 pulses. Next, the cells were plated in T75 flasks for 48 hours, and then sorted for GTP positive cells using Beckman Coulter MoFlo XDP. The sorted cells were plated in 96-well plates. After 10 days, half of the cells were used for genotyping. To examine the presence of indels after insertion of TALENs, genomic DNA fragments flanking the TALEN cleavage site were amplified by PCR Genomic DNA from the cultured cells was isolated using cell lysis buffer, and then used for PCR. PCR for amplification was performed under the following conditions: initial denaturation at 95° C. for 2 min, followed by 32 cycles, each consisting of denaturation at 94° C. for 30 sec, annealing at 55° C. for 30 sec, and extension at 72° C. for 30 min (see the PCR primer set in Table 1 below). The predicted sizes of the PCR products were 417 bp for IL2RG and 426 bp for RAG2. The PCR products were sequenced to identify the presence of indels.

Example 2: Somatic Cell Nuclear Transfer

To produce SCNT embryos, sow oocytes were purchased from ART (Madison, Wis.). The oocytes were shipped overnight in a maturation medium (TCM199 with 2.9 mM Hepes, 5 μg/ml insulin, 10 ng/ml EGF, 0.5 μg/ml p-FSH, 0.91 mM pyruvate, 0.5 mM cysteine, 10% porcine follicular fluid, and 25 ng/ml gentamicin). After 24 hours, the oocytes were transferred to a fresh medium. After 40-42 hours of maturation, cumulus cells were removed from the oocytes by vortexing in the presence of 0.1% hyaluronidase. During manipulation, the oocytes were placed in a manipulation medium supplemented with 7.0 μg/ml of cytochalasin B. The polar body along with a portion of the adjacent cytoplasm, probably containing the metaphase II plate, was removed, and donor cells were placed in the perivitelline space using a thin glass capillary.

Next, the reconstituted embryos were fused in a fusion medium (0.3 M mannitol, 0.1 mM $CaCl_2$, 0.1 mM $MgCl_2$, 0.5 mM Hepes) by two DC pulses (1-sec interval) at 1.2 kV/cm for 30 μsec using BTX Electro Cell Manipulator (Harvard Apparatus). After fusion, the fused embryos were fully activated with 200 μM thimerosal for 10 min and 8 mM dithiothreitol for 30 min under dark conditions. Then, the embryos were incubated with 0.5 μM scriptaid (that is a histone deacetylase inhibitor) in Porcine Zygote Media 3 $(PZM3)^3$ for 14-16 hours. The next day, the SCNT embryos were transferred into surrogates. For blastocyst transfer, the embryos were washed from scriptaid and cultured in PZM3 in the presence of 10 ng/ml of CSF2 for additional five days. The SCNT embryos were surgically transferred into the ampullary-isthmic junction of surrogates.

Example 3: Immunohistochemistry (IHC)

For IHC, tissues fixed in neutral buffer with 10% formalin were used. The tissues were placed on slides for IHC.

Endogenous peroxidase activity was first blocked in 3% hydrogen peroxidase. The samples were pretreated with Borg Decloaker, and then blocked in background Sniper solution. After washing, the samples were incubated with primary antibodies specific either for B cells (CD79A; Diagnostic Biosystems-# Mob118, 1:100) or for T cells (CD3; DAKO-# A0452, 1:400). After incubation, the samples were washed and incubated with HRP-conjugated secondary antibodies. Then, the samples were stained with Romulin Red Chromogens to visualize the signals. In addition, the samples were also stained with IP FLX Hematoxylin to provide backgrounds. The Borg, Sniper, Romulin Red and IP FLX hematoxylin were all purchased from Biocare (Concord, Calif.). All micrographs were acquired using a Zeiss Axiophot microscope (Carl Zeiss, Oberkochen, Germany) equipped with an Olympus DP70 high-resolution digital microscope camera (Olympus, Center Valley, Pa.).

Example 4: Flow Cytometry

The spleens from euthanized wild-type and biallelic piglets were collected into RPMI-1640 medium (Mediatech, Inc., Manassas, Va.) supplemented with 10% fetal bovine serum, minced with a scalpel blade, aspirated several times using a 20 gauge needle, and then passed through a 70 μm nylon mesh cell strainer (BD Biosciences, San Jose, Calif.). The splenocyte suspension was then incubated for 15 minutes with Pharm Lyse solution (BD Biosciences) to lyse erythrocytes, and then pelleted at 200×g for 5 minutes. After discarding the supernatant, the pellets were resuspended in cold staining buffer (BD Pharmingen), and the cells were counted on a hemacytometer. Then, the cells were divided into aliquots of $5\times10^6$ cells in 200 μL staining buffer. FITC-labeled mouse anti-pig CD21, mouse anti-pig CD 3ε, and mouse anti T-2 mycotoxin IgGlk (Isotype control group) (SouthernBiotech, Birmingham, Ala.) were added to the cells in an amount of $0.5\ \mu g/1\times10^6$ cells, and then incubated at 4° C. under dark conditions for 30 minutes. The cells were then washed twice and resuspended in fresh staining buffer. The cells were analyzed using a CyAn ADP flow cytometer (Beckman Coulter, Brea, Calif.) in a Cell and Immunobiology Core facility at the University of Missouri. Data were analyzed using Summit v4.3 software (Beckman Coulter).

Example 5: Off-Target Analysis

To identify putative off-target sequences from the TALENs used in the present invention, bioinformatics tools were used to identify sequences similar to each TALEN binding site from the most recent pig genome assembly (S scrofa10.2). PCR primers were designed flanking the most likely off-target sites based on the number of nucleotide differences. These regions were amplified in the founder animals and tested for off-targeting events using a Surveyor nuclease assay (Table 2 below). After PCR amplification, 300-500 ng of the PCR products (10-15 μl) were transferred into fresh tubes, and then denatured and reannealed according to a thermocycler program (95° C. for 2 min, 95° C. to 85° C. at a rate of −2° C./second, 85° C. to 25° C. at a rate of −0.1° C./second, 4° C. indefinitely). 1 μl of Surveyor nuclease and 1 μl of Surveyor enhancer were added thereto, and then incubated at 42° C. for 30 minutes. Then, the reactions were immediately placed on ice, and 6× Surveyor nuclease stop buffer and 6× dye were added to the reactions. The samples were electrophoresed on 2.0% agarose gel.

TABLE 1

| Gene | Primers | Product |
| --- | --- | --- |
| IL2RG | F: CTGGACTATTAGAAGGATGTGGGC (SEQ ID NO: 2); R: ATATAGTGGGAAGCCTGGGATGCT (SEQ ID NO: 3) | 417 |

Table 1 above shows the primers used for genotyping of IL2RG mutants induced by TALENs.

TABLE 2

| Gene | Abbreviation | Primers | Product |
| --- | --- | --- | --- |
| Leucine-rich repeats and IQ motif containing 1 | LRRIQ1 | F: CGTTTGTTAAAACTGC AGCATA (SEQ ID NO: 4); R: TTTTGCTTCCCTTTCC TTCC (SEQ ID NO: 5) | 150 |
| Basonuclin 2 | BNC2 | F: AGCCAGAGGAAGGGGT TTTA (SEQ ID NO: 6); R: GGTTAACCAGCTCAGG CAAC (SEQ ID NO: 7) | 199 |
| Solute carrier family 17 (anion/sugar transporter), member 5 | SLC17A5 | F: GTCTGGTTGCAGCTCA AGGT (SEQ ID NO: 8); R: GCCACTGTGGACTCTAG AGGAT (SEQ ID NO: 9) | 369 |
| Zinc finger protein 334 | ZNF334 | F: ATTCACACAGGGGAGAA ACG (SEQ ID NO: 10); R: GTGGAAATTTTTCCCCC ATT (SEQ ID NO: 11) | 233 |
| Titin | TTN | F: CTTTGGACCTGCCCACT TT (SEQ ID NO: 12); R: GGATGTGTGATCGGTTC CAT (SEQ ID NO: 13) | 228 |
| Progesterone receptor membrane component 2 | PGRMC2 | F: TGAGGGAGAGAGGAGAC CTG (SEQ ID NO: 14); R: CTAGGGGAAGGAAAGGG ATG (SEQ ID NO: 15) | 238 |
| Arginine vasopressin receptor 2 | AVPR2 | F: GGCGTACATGCCTACCA TCT (SEQ ID NO: 16); R: CTGTCCACGGTCTTTGT GG (SEQ ID NO: 17) | 246 |
| Coiled-coil domain containing 18 | CCDC18 | F: TTCTCCCAACCCCATTT ACA (SEQ ID NO: 18); R: CCTGAGTTGAACCAGCA CCT (SEQ ID NO: 19) | 405 |
| Zinc finger, SWIM-type containing 2 | ZSWIM2 | F: AAAAAGTTCTTCCTGTT TTGACAGA (SEQ ID NO: 20); R: TGGTTATTCCAC CAATGCAA (SEQ ID NO: 21) | 150 |

Table 2 above shows the primer sets used to identify off-site targeting of porcine IL2RG.

TABLE 3

IL2RG Embryo Transfer List

| ET Date | Donor cell | Number of embryos transferred | Day of heat | Results |
| --- | --- | --- | --- | --- |
| Oct. 12, 2012 | Korean IL2RG 010, 13, 15 | 216 | 1 | 1 female |
| Feb. 25, 2013 | Korean IL2RG 53-1 | 96 | 4 | Cycled |
| Feb. 25, 2013 | Korean IL2RG 53-1 | 179 | 4 | Cycled |
| Apr. 2, 2013 | Korean IL2RG 53-1 | 35 Blast | 6 | Cycled |
| Apr. 9, 2013 | Korean IL2RG 53-1 | 35 Blast | 4 | Cycled |
| Apr. 10, 2013 | Korean IL2RG 53-1 | 48 Blast | 4 | — |
| Apr. 23, 2013 | Korean IL2RG 53-1 | 51 Blast | 5 | — |
| Apr. 25, 2013 | Korean IL2RG 53-1 | 187 | 1 | — |
| Apr. 26, 2013 | Korean IL2RG 53-1 + RAG2 | 243 | 0 | — |

Table 3 above shows the nuclear transfer efficiencies obtained in the present invention.

Accession No.

Name of depository authority: Korea Research Institute of Bioscience and Biotechnology;

Accession No.: KCTC 12497;

Deposition Date: Oct. 2, 2013.

The invention claimed is:

1. A method for producing an immune cell-deficient transgenic miniature pig having an allelic mutation that disrupts the interleukin-2 receptor gamma (IL2RG) gene, the method comprising the steps of:
   (a) introducing into a miniature pig somatic cell a TALEN that recognizes a TALEN recognition sequence, wherein the TALEN recognition sequence is nucleotides 1-19 and 32-50 of SEQ ID NO:1 of the IL2RG gene on chromosome X of the pig somatic cell, and wherein said TALEN produces a deletion of nucleotides 26-29 of SEQ ID NO:1 of the IL2RG gene, and wherein said deletion results in an allelic mutation represented by SEQ ID NO:24 and a premature stop codon in the IL2RG gene;
   (b) producing a nuclear transfer miniature pig embryo by introducing the pig somatic cells produced in step (a) into enucleated miniature pig oocyte; and
   (c) transferring the embryo into a surrogate gilt and allowing the embryo to gestate to term to produce a transgenic miniature pig comprising a disruption in the IL2RG gene on chromosome X, wherein said disruption ablates IL2RG expression, and wherein the transgenic pig is immune cell deficient.

2. A method of claim 1, wherein said introducing of said TALEN comprises transfecting the miniature pig somatic cell with a vector encoding said TALEN.

3. A transgenic, cloned, immune cell-deficient miniature pig produced by the method of claim 1.

4. A cell from the transgenic, cloned immune cell-deficient miniature pig of claim 3.

5. The cell of claim 4, wherein the cell is a fibroblast cell line having accession number KCTC12497.

* * * * *

SEQUENCE LISTING

```
<160> NUMBER OF SEQ ID NOS: 36

<210> SEQ ID NO 1
<211> LENGTH: 50
<212> TYPE: DNA
<213> ORGANISM: Sus scrofa

<400> SEQUENCE: 1
tcagtgtttt gtgttcaatg ttgagtacat gaattgcact tggaacagca            50

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggactatt agaaggatgt gggc                                        24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atatagtggg aagcctggga tgct                                        24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtttgttaa aactgcagca ta                                          22
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttttgcttcc ctttccttcc                                             20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agccagagga aggggtttta                                             20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggttaaccag ctcaggcaac                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtctggttgc agctcaaggt                                             20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccactgtgg actctagagg at                                          22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attcacacag gggagaaacg                                             20
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtggaaattt ttcccccatt                                              20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctttggacct gcccacttt                                               19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggatgtgtga tcggttccat                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgagggagag aggagacctg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctaggggaag gaaagggatg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcgtacatg cctaccatct                                              20

<210> SEQ ID NO 17
```

<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgtccacgg tctttgtgg                                                19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttctcccaac cccatttaca                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctgagttga accagcacct                                               20

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaaaagttct tcctgttttg acaga                                         25

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tggttattcc accaatgcaa                                               20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcagtgtttt gtgttcaat                                                19

<210> SEQ ID NO 23
<211> LENGTH: 20

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaattgcact tggaacagca                                                  20

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tcagtgtttt gtgttcaatg ttgagtgaat tgcacttgga acagca                     46

<210> SEQ ID NO 25
<211> LENGTH: 50
<212> TYPE: DNA
<213> ORGANISM: Sus scrofa

<400> SEQUENCE: 25
tcagtgtttt gtgttcaatg ttgagtacat gaattgcact tgcaacagca                 50

<210> SEQ ID NO 26
<211> LENGTH: 50
<212> TYPE: DNA
<213> ORGANISM: Sus scrofa

<400> SEQUENCE: 26
ataatgcagc tgtaaaaatt caagctaaat ataaagcact tgtggcctac                 50

<210> SEQ ID NO 27
<211> LENGTH: 50
<212> TYPE: DNA
<213> ORGANISM: Sus scrofa

<400> SEQUENCE: 27
tcagtgtttt gtgtttcccc cacatgatgt gtcagaaacg aaagccagcc                 50

<210> SEQ ID NO 28
<211> LENGTH: 50
<212> TYPE: DNA
<213> ORGANISM: Sus scrofa

<400> SEQUENCE: 28
ttcttgtttt gtcctgtttg ttcaacacta cctgtaacat tttaactaaa                 50

<210> SEQ ID NO 29
<211> LENGTH: 50
<212> TYPE: DNA
<213> ORGANISM: Sus scrofa

<400> SEQUENCE: 29
tcagtgtgga aaattttttat gtactgaagc agccctcatg gcacatcaga                50

<210> SEQ ID NO 30
<211> LENGTH: 49
<212> TYPE: DNA
<213> ORGANISM: Sus scrofa
```

<400> SEQUENCE: 30
ctacgatggt ggtggaatgg ctccacgatg gaaagccact tgaagcagc        49

<210> SEQ ID NO 31
<211> LENGTH: 50
<212> TYPE: DNA
<213> ORGANISM: Sus scrofa

<400> SEQUENCE: 31
ttggggtttt gtcagggaaa agaaaaaact ttatttctaa gaaatctttg        50

<210> SEQ ID NO 32
<211> LENGTH: 50
<212> TYPE: DNA
<213> ORGANISM: Sus scrofa

<400> SEQUENCE: 32
gaagcggtag gtggcatccc aggccagctg gggcagcact tggaacagag        50

<210> SEQ ID NO 33
<211> LENGTH: 50
<212> TYPE: DNA
<213> ORGANISM: Sus scrofa

<400> SEQUENCE: 33
ctttctgaag aattattgca ggacttaaaa aaaatgcaac tggaacaacc        50

<210> SEQ ID NO 34
<211> LENGTH: 50
<212> TYPE: DNA
<213> ORGANISM: Sus scrofa

<400> SEQUENCE: 34
ttatatataa cttgtccatc aatagggcat gaattgcatt ggtggaataa        50

<210> SEQ ID NO 35
<211> LENGTH: 23
<212> TYPE: DNA
<213> ORGANISM: Sus scrofa

<400> SEQUENCE: 35
tcaatgttga gtacatgaat tgc        23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other -continued

```
<400> SEQUENCE: 36
tcaatgttga gtgnntngnn tgn                                        23
```